United States Patent [19]

Cumming et al.

[11] Patent Number: 4,793,344

[45] Date of Patent: Dec. 27, 1988

[54] METHOD FOR PREPARING CORNEAL DONOR TISSUE FOR REFRACTIVE EYE SURGERY

[75] Inventors: J. Stuart Cumming, Anaheim; J. Roberts Fosberg, S. Laguna, both of Calif.

[73] Assignee: Recore, Inc., Irvine, Calif.

[21] Appl. No.: 115,882

[22] Filed: Nov. 2, 1987

[51] Int. Cl.$^4$ .............................................. A61F 17/32
[52] U.S. Cl. ................................ 128/305; 128/303.1; 623/6
[58] Field of Search ................. 128/303.1, 305; 623/5, 623/6; 34/5

[56] References Cited

U.S. PATENT DOCUMENTS

| | | | |
|---|---|---|---|
| 4,346,482 | 8/1982 | Tennant et al. | 128/305 |
| 4,619,257 | 10/1986 | Linner et al. | 128/303.1 |
| 4,660,556 | 4/1987 | Swinger et al. | 128/305 |
| 4,662,881 | 4/1987 | Nordan | 623/5 |
| 4,664,110 | 5/1987 | Schanzlin | 128/303.1 |
| 4,676,070 | 6/1987 | Linner | 34/5 |
| 4,676,790 | 1/1987 | Kern | 128/303.1 |
| 4,724,522 | 2/1988 | Belgorod | 128/303.1 |

Primary Examiner—Max Hindenburg
Attorney, Agent, or Firm—Keith D. Beecher

[57] ABSTRACT

Method for preparing corneal donor tissue preferably from animal sources, or other living species, such as pigs, for refractive eye surgery resulting in lenticules of predictable lens power and which prevent immunologic rejection. The method inludes the chemical treatment of the corneal donor tissue by a fixative agent, such as gluteraldhyde, which neutralizes immune response and which cross-links the tissue to prevent swelling. The tissue is stabilized for long periods by the chemical treatment and does not necessarily require freezing for lathing. The method allows for the preparation and storage of large numbers of corneal lenticules in a variety of predictable powers and sizes, preferably with preplaced sutures, for subsequent eye surgery, particularly for epikeratophakia grafts and penetrating keratoplasty (corneal transplants).

10 Claims, No Drawings

METHOD FOR PREPARING CORNEAL DONOR TISSUE FOR REFRACTIVE EYE SURGERY

BACKGROUND OF THE INVENTION

The correction of refractive errors of the eye by the attachment of donor material directly onto the corneal surface has been carried out in the prior art for several years. The most accepted technique is known as "epikeratophakia". This technique involves the formation of a ring-shaped trough in the recipient corneal bed, and the placement and suturing of the donor material onto the optical center of the cornea with its edges fitting into the trough. This technique requires that the epithelium of the cornea grow over the resulting lenticule which attaches itself to the surface of the lenticule.

Another prior art procedure for refractive correction of the eye is a technique referred to as "intralamellar insertion". This latter procedure involves the insertion of the lenticule into a pocket prepared in the corneal stroma.

Both of the foregoing techniques require a material which transmits light, and which will allow for the passage of oxygen, glucose, and amino acids for the metabolic and nutritional requirements of the cornea. A lenticule freeze-lathed from human tissue, or from a material of high water content such as hydroxyethylmethylmetha-crylate, usually used at the present time for these prior art procedures. However, such materials suffer from unpredictability regarding the final shape of the lenticule, and therefore regarding the refractive correction of the surgical procedure.

Since the corneal stroma is maintained in a partially dehydrated state (REF), by the fluid barrier provided by the corneal epithelium, and the fluid pumping action provided by the corneal endothelium, the lenticule material is also subject to dehydration, which is not totally predictable.

In addition, the initial cutting of the presently used corneal donor material is subject to variation depending upon the water content of the material at the time of freezing and lathing. There is, therefore, a need for a lenticule material which can be cut predictably, and which will provide a known lenticule shape regardless of minor variations in the hydration of the donor corneal tissue. There is also a need to be able to measure the optical power of the lenticule before it is sutured into the cornea.

Accordingly, a major problem which is encountered when human corneal tissue is used to form the lenticule is its unpredictability, as discussed above. Specifically, it is not presently feasible to determine the refractive power of the resulting lenticule prior to its attachment to the eye of the recipient. This problem is compounded by the fact that if a number of human corneal tissues are lathed to a particular thickness, they tend to exhibit different refractive powers. These problems lead to substantial trial and error in present-day refractive surgical procedures, often requiring multiple attempts to form a lenticule, with the correct refractive power attached to the cornea of the patient's eye.

The method of the present invention, in one of its embodiments, utilizes specially treated animal corneal tissue, obtained preferably from pigs, such as suggested, for example, in U.S. Pat. No. 4,346,482 which issued Aug. 31, 1982, in the names of Jerald L. Tennant et al. The specially treated pig corneal tissue has a much higher predictable refractive power than the human tissue when lathed to a particular thickness. Moreover, the specially treated pig corneal tissue is clearer than human corneal tissue and may be subjected to pre-testing before attachment to the eye of the patient to determine the refractive power of the tissue, so that the proper tissue may be selected for a particular recipient.

Accordingly, the present invention makes possible the creation of a bank of donor tissues having pre-established refractive powers, and which may be conveniently selected and used for refractive eye surgery. An important aspect of the invention involves the treatment of the donor tissue with a fixative agent, such as gluteraldehyde, which not only neutralizes the immune response, and cross-links the tissue to prevent swelling, but which also enables the tissues to be stored for long periods of time without deterioration. Another aspect of the invention is the preparation of the lenticule with pre-placed sutures to facilitate tee surgery and reduce distortion and astigmatism.

Accordingly, an objective of the invention is to provide a method for fabricating a lenticule for use in refractive eye surgery which is formed from readily available donor tissue, and which comprises the step of treating the tissue with a fixative agent such as gluteraldehyde, so that the tissue will not induce a rejection response of the recipient immune system, and which additionally enables the tissue to be stored for long periods of time without degradation.

Another object of the invention is to provide such a method in which the tissue can be prepared in sufficient numbers to meet implantation requirements without the need to await the availability of the donor tissues.

Another objective of the invention is to provide a method for fabricating the lenticule to a selected refractive power which may be established with a high degree of precision prior to the attachment of the lenticule to the eye of the patient.

Yet another objective of the invention is to provide a method for fabricating the lenticule which does not change shape upon change of the water content during the fabrication process or upon change of the water content of the recipient cornea, and which will maintain its clarity in the eye of the patient.

DETAILED DESCRIPTION OF A PREFERRED EMBODIMENT OF THE METHOD OF THE INVENTION

A preferred method for preparing donor tissue lenticules in accordance with the invention comprises the following steps:

1. Removal of the corneal tissue from a donor, such as a pig, and the immediate fixation of the tissue in a solution containing gluteraldehyde. This cross-links the collagen fibrils and prevents swelling of the tissue. A preferred solution is one containing 0.5%–4% gluteraldehyde in a 0.1M phosphate buffer. Fixation times of up to two weeks have been found to be appropriate.

2. Washing the tissue in a physiological solution, such as 0.1M phosphate buffer. Several replacements of the solution over a period of days are desirable to remove detectable traces of gluteraldehyde. Washing may be carried out at 4° C. in a refrigerator to prevent bacterial growth.

3. Lathing the tissue. This can be accomplished by several means, including freeze-lathing and vacuum-lathing. One technique which is particularly useful is shaping by means of an ablative laser, such as an excimer laser at 193 nm. This technique results in a surface which is smooth and which can be re-healed rapidly. The lenticules are lathed to desired thicknesses depending upon the refractive powers required of the various lenticules. The lathed lenticules may be stored in formaldehyde (4%).

4. Pre-placement of sutures. This may be accomplished far more readily during manufacture than in the surgical suite, and it results in a symmetrical pattern of ties which allows the corneal lenticule to be fastened to the recipient surface without introducing undesired astigmatism.

Although animal corneal tissue obtained, for example, from pigs has been referred to above, the donor corneal tissue may be derived from a variety of animals, or other living species, including, but not limited to pigs, cows, rabbits, cats, dogs, primates, cetacean dolphins, or other warm blooded animals, or chondrychthes, sharks, and soon.

Although gluteraldehyde has been suggested as the fixative solution, formaldehyde, or other aldehyde groups may be used. Moreover, the fixative may contain acrolein, or other substances which react with protein or glycoprotein in the donor tissue to prevent an immune response.

The oblative laser may be used to shape one or both surfaces of the lenticule. The lenticule may be fabricated with a cylindrical, as well as spherical correction, if so desired, in order to correct astigmatism.

It will be appreciated that although a preferred embodiment of the process of the invention has been described, modifications may be made which are intended to be covered in the following claims.

We claim:

1. A method for fabricating a corneal tissue for use in refractive eye surgery which comprises the following steps:
    (a) removing the corneal tissue from a donor;
    (b) placing the tissue in a fixative solution for a selected time interval to cross-link the collagen fibrils in the tissue and to prevent swelling of the tissue; and
    (c) lathing the tissue to provide a lenticule of a selected shape and thickness.

2. The method defined in claim 1, in which the fixative solution contains gluteraldehyde.

3. The method defined in claim 1, in which the fixative solution contains substantially 0.5%–4% gluteraldehyde in 0.1M phosphate buffer.

4. The method defined in claim 1, in which the selected time interval in which the tissue is placed in the fixative solution is up to two weeks.

5. The method defined in claim 1, and which includes the step of washing the corneal tissue in a physiological solution prior to lathing.

6. The method defined in claim 5, in which the physiologccal solution includes 0.1M phosphate buffer.

7. The method defined in claim 1, and which includes the step of attaching sutures to the lenticule after lathing to permit the lenticule to be attached to the recipient surface without any tendency to introduce astigmatism.

8. The method defined in claim 1, in which the lathing is carried out with the tissue in a frozen state.

9. The method defined in claim 1, in which the lathing is carried out with the tissue in a non-frozen state.

10. The method defined in claim 1, in which the lenticule is shaped with an eximer laser.

* * * * *